United States Patent
Weissberg et al.

(10) Patent No.: US 6,241,711 B1
(45) Date of Patent: Jun. 5, 2001

(54) THERAPEUTIC FACE AND EYE MASQUE

(75) Inventors: Gloria Weissberg; Tina Alster, both of Washington, DC (US); Felix Franks, Cambridge (GB); William Mallow, Helotes, TX (US)

(73) Assignee: SkinVestment, LLC, Washington, DC (US)

( * ) Notice: Subject to any disclaimer, the term of this patent is extended or adjusted under 35 U.S.C. 154(b) by 0 days.

(21) Appl. No.: 09/014,677

(22) Filed: Jan. 28, 1998

(51) Int. Cl.⁷ ..................................................... A61F 7/00
(52) U.S. Cl. .......................... 604/291; 604/303; 607/109
(58) Field of Search .................... 604/289, 290, 604/291, 303; 607/109, 108; D24/34, 43, 36, 208, 200

(56) References Cited

U.S. PATENT DOCUMENTS

| | | |
|---|---|---|
| D. 170,499 | 9/1953 | Gloeckler . |
| D. 182,389 | 3/1958 | Sisco . |
| D. 296,941 | 7/1988 | Ieutholt et al. . |
| D. 320,457 | 10/1991 | Dickinson . |
| D. 332,310 | 1/1993 | Ahlen . |
| 1,167,481 | 1/1916 | Cupeland . |
| 2,434,198 | 1/1948 | Duma . |
| 2,626,343 | 1/1953 | Fogel et al. . |
| 2,635,175 | 4/1953 | Hodge . |
| 2,796,903 | 6/1957 | Gazelle . |
| 3,606,890 | 9/1971 | Gilbert . |
| 3,762,419 | 10/1973 | Walters . |
| 3,871,376 | 3/1975 | Kozak . |
| 4,243,041 | 1/1981 | Paul . |
| 4,527,565 | 7/1985 | Ellis . |
| 4,530,220 | 7/1985 | Nambu et al. . |
| 4,559,047 | 12/1985 | Kapralis et al. . |
| 4,614,189 | 9/1986 | MacKenzie . |
| 4,671,267 | 6/1987 | Stout . |
| 4,854,319 | * 8/1989 | Tobin . |
| 4,920,963 | 5/1990 | Brader . |
| 5,020,536 | 6/1991 | Keen . |
| 5,119,812 | 6/1992 | Angelo . |
| 5,145,748 | 9/1992 | Gaidis et al. . |
| 5,163,425 | 11/1992 | Nambu et al. . |
| 5,178,143 | 1/1993 | Kwak et al. . |
| 5,211,949 | 5/1993 | Salyer . |
| 5,274,865 | * 1/1994 | Takehashi ................................ 5/644 |
| 5,314,456 | 5/1994 | Cohen . |
| 5,356,426 | 10/1994 | Delk et al. . |
| 5,393,462 | * 2/1995 | Avery .................................... 604/291 |
| 5,514,170 | 5/1996 | Mauch . |

* cited by examiner

Primary Examiner—John G. Weiss
Assistant Examiner—David J. Cho
(74) Attorney, Agent, or Firm—Kenyon & Kenyon

(57) ABSTRACT

A face masque that applies cooling therapy to facial features of a patient. The masque is formed of two nylon or plastic layers that define a closed interior space and filled with a cooling medium that includes water, glycerin and hydroxyethyl cellulose. The masque controls the rate of heat dissipation from a user based upon the heat capacity, mass, rheology and composition of the materials used. The masque is lighter than conventional water-filled ice packs. It remains unfrozen and malleable even when cooled to sub-zero temperatures at which water-filled packs would freeze solid. The masque readily conforms to facial features due to the materials used, thereby contributing to improved comfort on the part of a user. Further, the masque possesses improved cooling therapy because it remains cold for longer periods of time relative to water-filled ice packs. Optionally, the masque accommodates eye inserts placed between a main body of the masque and recesses of the patient's eyes. Also, the masque may be provided with a cloth sheath separating the nylon or plastic layers from the patient's face.

28 Claims, 2 Drawing Sheets

THERAPEUTIC FACE AND EYE MASQUE

RELATED APPLICATION

The present invention benefits from priority of a U.S. patent application, entitled "Therapeutic Face and Eye Masque," Ser. No. unknown, filed Oct. 29, 1997 naming Gloria Weissberg, Tina Alster and Felix Franks as inventors, the disclosure of which is incorporated herein by reference.

BACKGROUND OF THE INVENTION

The present invention relates to a face masque that provides cooling therapy to patients recuperating from facial trauma such as surgery or injury. More particularly, the invention provides a face masque that is light in weight, that remains flexible at sub-zero temperatures and that remains cold over longer periods than conventional water-filled ice packs.

It is well known in the medical profession that cooling of bodily tissues immediately after physical trauma or injury is necessary to reduce swelling of such tissues. A variety of ice packs and related devices are commercially available to provide such therapy. Therapy of facial trauma, however, involves unique considerations.

Human beings are much more sensitive in the areas of the face and head in other areas of the body. An application of direct pressure to the face, particularly after surgery, can cause a patient to suffer additional discomfort beyond that incurred by the surgery. Traditional ice packs possess many characteristics that are disadvantageous when applied to patients who have suffered facial trauma.

Traditional water-filled packs are heavy. The weight of the pack increases the patient's discomfort during recuperation.

Traditional water-filled cooling packs often are frozen solid when applied to a patient's face. As such, the ice pack does not mold to the patient's features. The solid nature of the ice pack causes discomfort until the ice pack has warmed to the point where the frozen water inside the ice pack has melted. The solid ice pack also may fail to provide cooling therapy uniformly because the frozen ice pack may not contact the patient's face in the absence of undue pressure.

Water-filled cooling packs do not remain cold for prolonged periods of time. The ability of a substance to store energy is termed "specific heat." It is well known that liquid water possesses a higher specific heat that frozen water. Accordingly, a cooling therapy that maintains water as a liquid below 0° C. would provide an improved cooling medium. While it is known to mix water with sodium chloride (NaCl) or ethylene glycol (an additive commonly used in automobile anti-freezes), the resultant mixtures obtained often are heavier than water. They, too, would cause increased discomfort to a patient who has suffered facial trauma. Although the solutions affect the specific heat of the water, the solutions may freeze. For example, an NaCl solution progressively freezes during cooling as the temperature of the solution approaches −21° C. Thus, the known solutions do not fully address the concerns raised when one tries to provide therapeutic cooling to the face of a patient.

The disadvantages of known ice packs are so great that medical practitioners have suggested alternatives to conventional ice packs. Patients have been advise to place bags of frozen vegetables on their faces to achieve the cooling therapy effect.

Certain inventors of the present invention had previously developed a face masque that improved upon the face masques of the prior art. As disclosed in a U.S. patent application, filed Oct. 29, 1997 (08/960,041), the improved face masque materially advanced the art by providing a face masque that was light weight, that conformed readily to a patient's features and that remained cold for prolonged periods of time. Although the face masque of the prior application are improved over conventional water-filled ice packs, the inventors believed that other coolants were available that improved upon their invention.

Accordingly, there is a need in the art for a facial cooling pack that provides prolonged cooling therapy over ice packs. Further, there is a need for such an cooling pack that possesses reduced weight and remains malleable at sub-zero temperatures.

SUMMARY OF THE INVENTION

The present invention provides a facial ice pack ("face masque") that applies cooling therapy uniformly to all facial features of a patient. The masque is formed of two nylon or plastic layers that define a closed interior space. The masque is filled with a cooling medium that includes water, glycerin and hydroxyethyl cellulose. The masque is lighter than conventional water-filled ice packs. It is malleable even when cooled at freezing temperatures associated with water. Further, the masque possesses improved cooling therapy because it remains cold for longer periods of time relative to water-filled ice packs of the same weight.

Optionally, the masque accommodates eye inserts placed between a main body of the masque and recesses of the patient's eyes. Also, the masque may be provided with a cloth sheath separating the nylon or plastic layers from the patient's face.

BRIEF DESCRIPTION

DETAILED DESCRIPTION OF THE DRAWINGS

Figure 1:
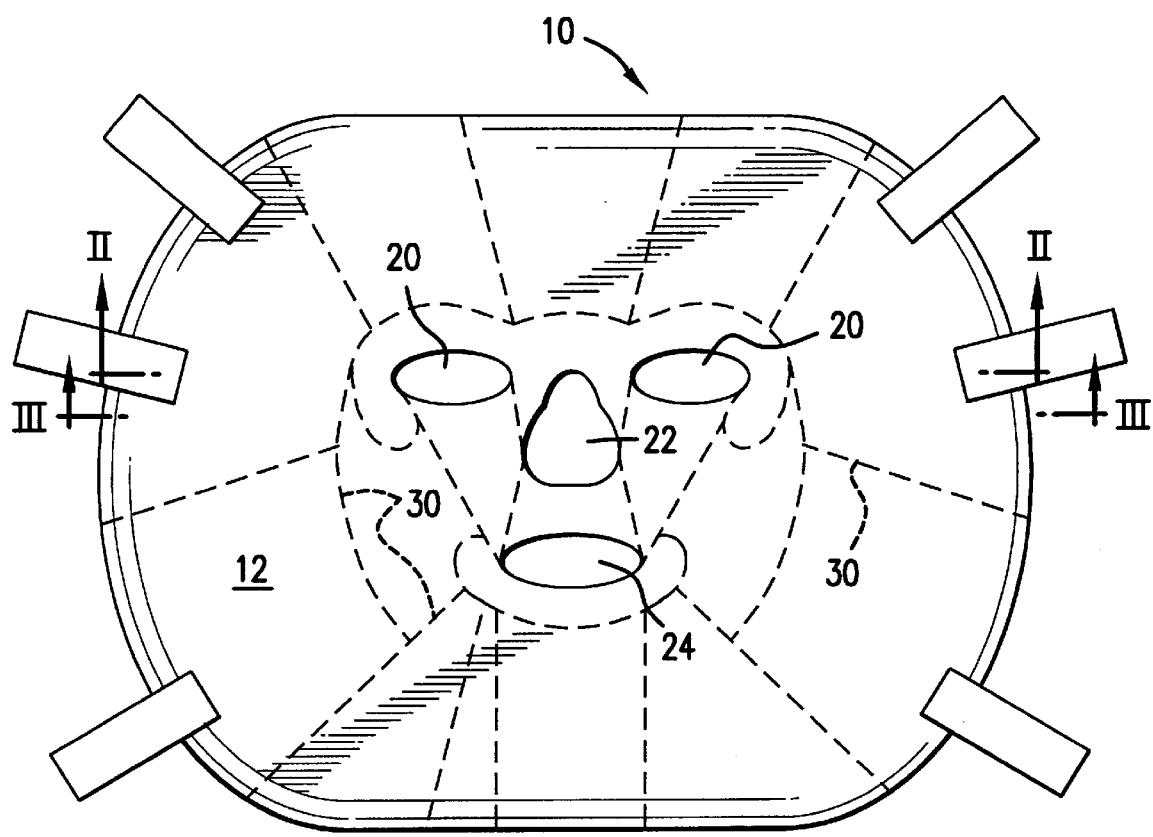
FIG. 1 is a frontal plan view of the face masque of the present invention.
Figure 2:
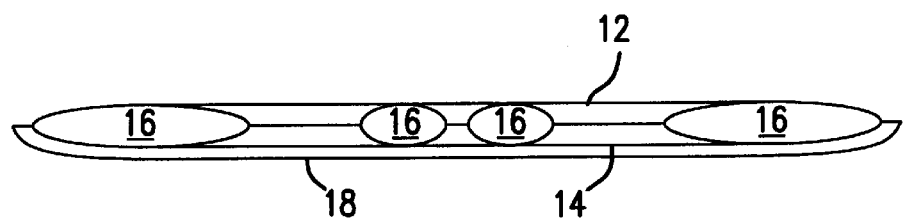
FIG. 2 is a sectional view of the masque of FIG. 1 without segmenting seals taken along the line II—II.

Turning now to FIGS. 1 and 2, there is shown a face masque 10 constructed in accordance with a first embodiment of the present invention. Masque 10 is formed of a first and a second layer 12 and 14 each of which possesses an elliptical shape having dimensions sufficient for the masque 10 to cover a human face. The first layer and second layer 12 and 14 form a closed interior space 16 therebetween. The layers 12 and 14 may be sealed together using techniques known in the art. Alternatively, the layers 12 and 14 may be formed as a continuous envelope structure. The masque 10 forms cutouts for eyes 20, nose 22 and mouth 24. The first and second layers 12 and 14 are fixed to each other along the edges of such cutouts to maintain the interior space 16 a closed one. A coolant is provided within the interior space 16.

In an embodiment, the first layers is vacuum formed and provided with a greater width than that of the second layer 14. The difference in widths to form a natural pocket structure. The interior space 16 defined thereby is larger than that of conventional ice packs and permits a greater volume of coolant to be provided therein. The degree to which the widths of the two layers differ determines the volume defined thereby.

The difference in width between the two layers 12, 14 also permits the masque 10 to mold to facial features of a patient more readily. Viewed from above, a patient's face is generally semi-circular. In use, the second layer 14 of the masque 10 is placed of the patient's face. When the masque 10 conforms to the semi-circular features of a patient, the greater width of the first layer 12 permits the first layer 12 to take a greater circumference than the second layer 14 without requiring external exertion of pressure. For this use, the masque 10 has a front and a back; the first layer 12 is the front of the masque 10 and the second layer 14 is the back of the masque 10 to be placed on the patient.

The first and second layers 12 and 14 are made of light, flexible plastic or nylon materials. For example, in an embodiment, the layers 12 and 14 may be formed of twelve thousandth gauge vinyl. Accordingly, the layers 12 and 14 possess sufficient flexibility to mold to a patient's facial features without requiring external pressure to be applied. Such flexibility permits the masque 10 to cool traumatized tissues without imposing additional trauma thereon.

Figure 3:
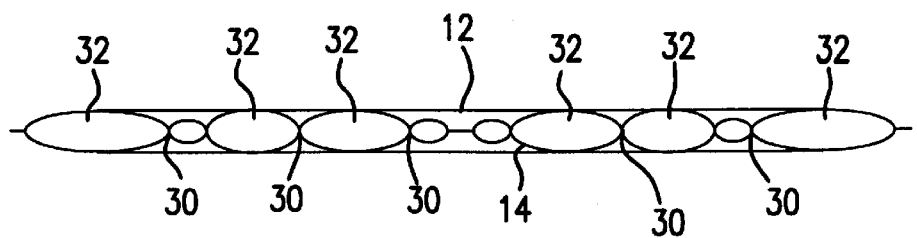
FIG. 3 is a sectional view of the masque of FIG. 1 with segmenting seals taken along the line III—III.

Optionally, the first and second layers 12 and 14 may be provided with interior segmenting seals 30 over the surface of the masque 10. Segmenting seals 30 join the first and second layers 12 and 14 together by glued or welded bonds. The segmenting seals 30 divide the closed interior space 16 into a plurality of "cells" 32 (shown in FIG. 3), interior chambers that inhibit migration of the coolant within the masque 10. The cells 32 may be closed entirely from each other. Alternatively, the cells 32 may be closed only partially to permit a slow migration of the coolant therebetween.

Optionally, the masque 10 possesses a cloth sheath 18 (shown in FIG. 2) that separates a plastic layer 14 of the masque from the face of the patient. From the patient's perspective, the cloth sheath 18 diffuses the effect of the cold masque while permitting the masque to cool the patient's face. The cloth sheath 18 possesses cutouts for the eyes, nose and mouth corresponding to the cutouts of the two layers 12 and 14. The cloth sheath 18 preferably is removably attached to the layer 14 to properly orient the eye cutouts of the sheath 18 with those of the layers. The cloth sheath 18 should be made from a material that may be washed by typical domestic laundry process. In a preferred embodiment, the cloth sheath 18 is made of a light cotton material. In use, the cloth sheath 18 may be disposable to be replaced by other cloth sheaths.

The face masque 10 may be provided with a plurality of straps 40 to mount the masque 10 on a patient's face. The straps 40 may be made of elastic Velcro to facilitate mounting and removal of the masque 10 from the patient.

The interior space 16, 32 is filled with a coolant that absorbs heat during use. The coolant contains water, glycerin and hydroxyethyl cellulose. The components are provided in such proportions that the coolant possesses the following characteristics: The coolant does not freeze at temperatures down to temperatures conventional to domestic freezers (−20° C.) and below, the components are completely compatible between −10 to 40° C., and the coolant possesses improved energy storage capacity over ice on a weight for weight basis.

The inventors experimented with a prototype of the coolant of the present invention. The coolant included a solution of 80 parts per volume (ppv) water, 20 ppv glycerin and 1½ parts per weight (ppw) hydroxyethyl cellulose. Twelve ounces of the coolant was formed into a sheet having a generally ¼ inch thickness and cooled to a temperature of −15° F. At such a temperature, the coolant remained plastic, soft and ductile.

The inventors simulated use of the coolant. They removed the coolant from the freezer and simulated its use on a patient. They placed an ordinary towel on a hot plate set to 100° F., a temperature that simulates inflamed facial tissues. They placed the cooled prototype on top of the hot plate and towel as a continuous mass. After four hours of exposure to the hot plate, the center of mass of the coolant had reached 65° F. At 65° F., a face masque would provide a cooling effect to a patient's face.

The 80/20/1½ solution of the prototype coolant subject to the above test weighs 12 ounces. This is considered a light-weight masque. Thus, the present invention provides a light-weight face masque that remains soft and pliable at temperatures of less than −15° F. and possess prolonged cooling effect.

Other combinations of the water, glycerin and hydroxyethyl cellulose were used. A coolant made of 75 ppv water, 25 ppv glycerin and 1½ ppw hydroxyethyl cellulose subjected to the same test above demonstrated similar benefits in that it remained pliable and soft at −15° F. When exposed to the 100° F. hot plate as described above, the coolant's center of mass reaches 65° F. after three hours, fifteen minutes.

Figure 4:
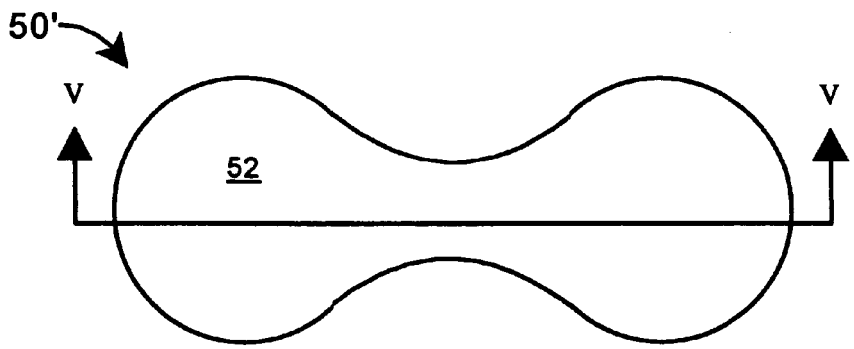
FIG. 4 is a frontal view of a first embodiment of an eye insert of the present invention.
Figure 6:
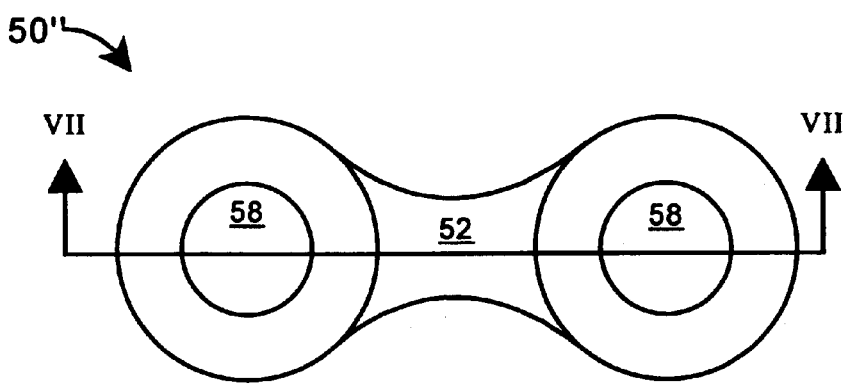
FIG. 6 is a perspective view of a second embodiment of an eye insert of the present invention.
Figure 7:
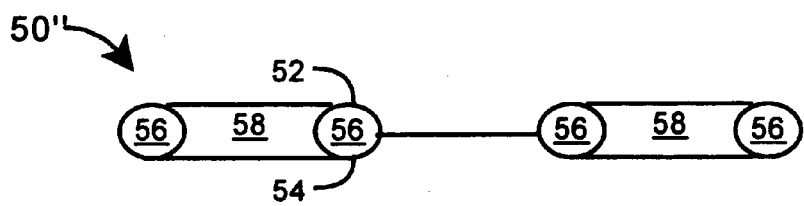
FIG. 7 is a sectional view of the eye insert of FIG. 6 taken along the line VII—VII.

The masque 10 may be adapted to receive optional eye inserts 50 to ensure that cooling therapy is applied in the area of the patient's eyes. An eye insert 50 is a pack placed over the patient's eyes before the masque 10 is applied. The surface of the eye insert 50 may be a flat disk as shown in FIG. 4 or may be donut-shaped with an unobscured center area 58 as shown in FIG. 6. The flat disk 50' obscures the patient's vision whereas the donut-shaped eye insert 50" does not.

Figure 5:
FIG. 5 is a sectional view of the eye insert of FIG. 4 taken along the line V—V.

As with the face masque 10, either eye insert 50 possesses first and second layers 52 and 54 defining a closed interior space 56. The first and second layers 52 and 54 may be continuously formed or may be bonded or welded together. The coolant occupies the interior space 56. The eye insert 50 may be enclosed by a cloth sheath 60 in a manner similar to the face masque 10 (shown in FIG. 5). For the donut-shaped eye insert 50", the cloth sheath 60 possesses a cutout to permit the patient to see through the eye insert (not shown).

The present invention provides cooling therapy for persons who have experienced facial injuries and for cooling therapy following laser, plastic, oral or dental surgery. The face masque provides a cold compress to reduce swelling following such trauma. Additionally, the face masque may be used for treatment of headaches, aches or pains and can be used additionally for cosmetic therapies. The face masque may be formed into a number of different shapes as the therapy dictates, such as flexible, cooled bandages and elastic stockings. The masque may be formed as a partial masque to conform to a portion of a patient's face. Additionally, the invention may by formed as a general purpose cooling pack to provide therapy to other body parts.

What is claimed is:

1. A face masque comprising:
   a first layer;
   a second layer, said first and second layers fixed together to form a closed interior space;

a coolant occupying the interior space, said coolant comprising 80 ppv water, 20 ppv glycerin, and 1½ ppw hydroxyethyl cellulose.

2. The face masque of claim 1, wherein the first and second layers form, in combination, eye, nose and mouth cutouts.

3. The face masque of claim 1, wherein the coolant is a viscous liquid at temperatures above −20° C.

4. The face masque of claim 1, where the coolant is a flexible, plastic solid at temperatures above −20° C.

5. The face masque of claim 1, wherein the face masque further comprises a cloth sheath covering one of the first and second layers.

6. The face masque of claim 1, wherein the face masque further comprises eye inserts to be placed between a patient's face and the masque.

7. The masque of claim 6, further comprising disk-shaped eye inserts.

8. The face masque of claim 6, further comprising donut-shaped eye inserts.

9. The face masque of claim 1, further comprising segmenting seals that join the first and second layers together, the segmenting seals dividing the interior space into a plurality of cells.

10. The face masque of claim 1, wherein the first layer has a greater width than the second layer.

11. The face masque of claim 1, wherein the first layer and second layer form a pouch structure.

12. The face masque of claim 1, wherein, when placed on generally semi-circular features of a patient, the first layer takes a greater circumference than the second layer.

13. A therapeutic cooling body, comprising:

a closed shell providing an interior space and a coolant provided in the interior space, said coolant comprising 80 ppv water, 20 ppv glycerin, and 1½ ppw hydroxyethyl cellulose.

14. The cooling body of claim 13, wherein the shell has a first and second layer, the first layer being of greater width than the second layer.

15. The cooling body of claim 13, further comprising a cloth sheath covering an exterior portion of the shell.

16. The cooling body of claim 13, wherein the coolant is a viscous liquid at temperatures above −20° C.

17. The cooling body of claim 13, wherein the shell forms a pouch structure.

18. The cooling body of claim 13, further comprising segmenting seals that join opposite sides of the shell together, the segmenting seals dividing the interior space into a plurality of cells.

19. A face masque comprising:

a first layer;

a second layer, said first and second layers fixed together to form a closed interior space; p1 a coolant occupying the interior space, said coolant comprising 75 ppv water, 25 ppv glycerin, and 1½ ppw hydroxyethyl cellulose.

20. The face masque of claim 19, wherein the coolant is a viscous liquid at temperatures above −20° C.

21. The face masque of claim 18, wherein the face masque further comprises eye inserts to be placed between a patient's face and the masque.

22. The face masque of claim 21, wherein the eye inserts are disk-shaped.

23. The face masque of claim 21, wherein the eye inserts are donut-shaped.

24. The face masque of claim 18, further comprising segmenting seals that join opposite sides of the shell together, the segmenting seals dividing the interior space into a plurality of cells.

25. A therapeutic cooling body, comprising:

a closed shell providing an interior space and a coolant provided in the interior space, said coolant comprising 75 ppv water, 25 ppv glycerin, and 1½ ppw hydroxyethyl cellulose.

26. The cooling body of claim 25, wherein the shell has a first and second layer, the first layer being of greater width than the second layer.

27. The cooling body of claim 25, wherein the shell forms a pouch structure.

28. The cooling body of claim 25, further comprising segmenting seals that join opposite sides of the shell together, the segmenting seals dividing the interior space into a plurality of cells.

* * * * *

UNITED STATES PATENT AND TRADEMARK OFFICE
CERTIFICATE OF CORRECTION

PATENT NO. : 6,241,711 B1
DATED : June 5, 2001
INVENTOR(S) : Weissberg et al.

It is certified that error appears in the above-identified patent and that said Letters Patent is hereby corrected as shown below:

Column 1,
Line 26, after "head" insert -- than --;
Line 46, delete "that" and insert -- than --.

Column 3,
Line 13, delete "of" and insert -- on --.

Column 5,
Line 17, before "masque" insert -- face --; delete "further comprising"
and insert -- wherein the eye inserts are --;
Line 18, delete "eye inserts".
Line 19, before "masque" insert -- face --; delete "further comprising" and insert
-- wherein the eye inserts are --;
Line 20, delete "eye" inserts".

Column 6,
Line 11, delete "p1"; "a coolant" begins a new paragraph.
Line 17, delete "18" and insert -- 19 --.
Line 24, delete "18" and insert -- 19 --.

Signed and Sealed this

Twentieth Day of August, 2002

Attest:

Attesting Officer

JAMES E. ROGAN
Director of the United States Patent and Trademark Office